US011037659B2

(12) United States Patent
Zhou et al.

(10) Patent No.: US 11,037,659 B2
(45) Date of Patent: Jun. 15, 2021

(54) DATA-ENRICHED ELECTRONIC HEALTHCARE GUIDELINES FOR ANALYTICS, VISUALIZATION OR CLINICAL DECISION SUPPORT

(71) Applicant: Siemens Healthcare GmbH, Erlangen (DE)

(72) Inventors: Xiang Sean Zhou, Exton, PA (US); Marcos Salganicoff, Bala Cynwyd, PA (US)

(73) Assignee: Siemens Healthcare GmbH, Erlangen (DE)

( * ) Notice: Subject to any disclaimer, the term of this patent is extended or adjusted under 35 U.S.C. 154(b) by 572 days.

(21) Appl. No.: 15/134,472

(22) Filed: Apr. 21, 2016

(65) Prior Publication Data

US 2016/0321402 A1    Nov. 3, 2016

Related U.S. Application Data

(60) Provisional application No. 62/153,791, filed on Apr. 28, 2015.

(51) Int. Cl.
*G16H 10/60* (2018.01)
*G16H 50/70* (2018.01)
*G16H 50/20* (2018.01)

(52) U.S. Cl.
CPC ............. *G16H 10/60* (2018.01); *G16H 50/20* (2018.01); *G16H 50/70* (2018.01)

(58) Field of Classification Search
CPC ....... G06F 19/322; G16H 50/70; G16H 50/20
See application file for complete search history.

(56) References Cited

U.S. PATENT DOCUMENTS

| | | | |
|---|---|---|---|
| 8,738,972 B1* | 5/2014 | Bakman | G06F 11/0712 |
| | | | 714/47.1 |
| 2006/0116908 A1* | 6/2006 | Dew | G06Q 50/22 |
| | | | 705/2 |
| 2008/0221923 A1* | 9/2008 | Shogan | G16H 50/20 |
| | | | 705/2 |
| 2009/0319338 A1* | 12/2009 | Parks | G06Q 30/02 |
| | | | 705/7.38 |
| 2013/0117280 A1* | 5/2013 | Donaldson | G06F 16/904 |
| | | | 707/748 |
| 2013/0166317 A1* | 6/2013 | Beardall | G06F 19/324 |
| | | | 705/2 |
| 2013/0311481 A1* | 11/2013 | Bhatt | G06F 17/30321 |
| | | | 707/741 |
| 2014/0058738 A1* | 2/2014 | Yeskel | G16H 50/50 |
| | | | 705/2 |
| 2014/0129246 A1* | 5/2014 | Vdovjak | G16H 10/20 |
| | | | 705/2 |
| 2014/0278462 A1* | 9/2014 | Jones | G16H 40/20 |
| | | | 705/2 |

(Continued)

*Primary Examiner* — Victoria P Augustine
*Assistant Examiner* — Jay M. Patel (57) ABSTRACT

A framework for visualization based on healthcare guidelines is described herein. In accordance with one aspect, a decision graph is generated based on healthcare guidelines. The nodes of the decision graph are populated with patient records. The framework may perform data analytics on patient records associated with at least one of the nodes to generate results, and further generate a visualization of the results.

17 Claims, 5 Drawing Sheets

(56) References Cited

U.S. PATENT DOCUMENTS

| | | | |
|---|---|---|---|
| 2015/0019569 A1* | 1/2015 | Parker | G06F 16/338 |
| | | | 707/748 |
| 2015/0066520 A1* | 3/2015 | Leon | G06F 19/3443 |
| | | | 705/2 |
| 2015/0081685 A1* | 3/2015 | Ashenfelter | G06F 16/9027 |
| | | | 707/723 |
| 2015/0082219 A1* | 3/2015 | Beck | G06Q 10/06 |
| | | | 715/771 |
| 2015/0120315 A1* | 4/2015 | Dann | G06F 19/00 |
| | | | 705/2 |
| 2015/0154361 A1* | 6/2015 | Barsoum | G16H 80/00 |
| | | | 705/3 |
| 2015/0227701 A1* | 8/2015 | Nicolaas | G16H 50/20 |
| | | | 705/2 |
| 2015/0269764 A1* | 9/2015 | McGill | G06T 13/20 |
| | | | 345/474 |
| 2015/0317337 A1* | 11/2015 | Edgar | G16H 50/70 |
| | | | 707/751 |
| 2016/0070876 A1* | 3/2016 | Warner | G16H 50/30 |
| | | | 705/3 |
| 2016/0092641 A1* | 3/2016 | Delaney | G16H 50/70 |
| | | | 705/3 |
| 2016/0098527 A1* | 4/2016 | Zhang | G16H 10/60 |
| | | | 705/3 |
| 2016/0103960 A1* | 4/2016 | Hume | G06Q 50/22 |
| | | | 705/2 |
| 2016/0110523 A1* | 4/2016 | Francois | G06Q 50/24 |
| | | | 705/2 |
| 2016/0217123 A1* | 7/2016 | Chulinin | G06K 9/03 |
| 2016/0283657 A1* | 9/2016 | Bhotika | G06F 19/321 |
| 2016/0306928 A1* | 10/2016 | Sherling | G06F 19/00 |

* cited by examiner

DATA-ENRICHED ELECTRONIC HEALTHCARE GUIDELINES FOR ANALYTICS, VISUALIZATION OR CLINICAL DECISION SUPPORT

CROSS-REFERENCE TO RELATED APPLICATION

The present application claims the benefit of U.S. provisional application No. 62/153,791 filed Apr. 28, 2015, the entire contents of which are herein incorporated by reference.

TECHNICAL FIELD

The present disclosure generally relates to data processing, and more particularly to data-enriched healthcare guidelines.

BACKGROUND

Healthcare guidelines assist physicians and other healthcare providers in making the most appropriate decisions for a specific clinical condition. Such guidelines are typically developed and published by medical centers, institutions and other organizations to enhance the quality and efficiency of care, and to achieve improved outcomes, more optimal healthcare delivery and justifiable healthcare expenditures. One type of healthcare guidelines is the appropriate use criteria (AUC), also known as appropriateness criteria. AUC are evidenced-based healthcare guidelines that specify when or how a procedure should be performed or used. An "appropriate" procedure is one for which the expected health benefits exceed the expected health risks by a wide margin in the context of available medical evidence and expert opinion. AUC have been undertaken for many medical fields, including but not limited to, echocardiography, radiology, dermatology, cardiology, dentistry, and so forth. Healthcare guidelines are often complex and difficult to follow. They are often qualitative and not sufficiently quantitative enough to generate structured data for computational analysis. Such guidelines are also typically incomplete and not personalized enough for a given patient.

SUMMARY

Described herein are systems and methods for visualization based on healthcare guidelines. In accordance with one aspect, a decision graph is generated based on healthcare guidelines. The nodes of the decision graph are populated with patient records. The framework may perform data analytics on patient records associated with at least one of the nodes to generate results, and further generate a visualization of the results.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to x-ray radiographs, MRI, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images and voxels for 3D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture or a 3D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

The terms "pixels" for picture elements, conventionally used with respect to 2D imaging and image display, and "voxels" for volume image elements, often used with respect to 3D imaging, can be used interchangeably. It should be noted that the 3D volume image is itself synthesized from image data obtained as pixels on a 2D sensor array and displays as a 2D image from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel" or "subject voxel" are used to indicate a particular image element as it is operated upon using techniques described herein.

A framework for analytics, visualization or clinical support based on data-enriched healthcare guidelines is described herein. In accordance with one aspect, the framework generates an electronic decision graph that represents a set of healthcare guidelines. The nodes of the decision graph may be populated or updated in substantially real time with actual patient records (or data). Data analytics tools may be invoked at each node to process the patient records for visualization, online learning, decision support, or other applications. The visualization based on the decision graph is advantageously easy for the user to read and follow, and becomes more quantitative and statistically powerful with more usage. In addition, the results from the data analytics tools may be presented to support healthcare decision-making for a particular patient, and/or enable retrospective evaluation of decisions made for a population or in an organization (e.g., hospital). These and other exemplary features and advantages will be described herein.

Figure 1:
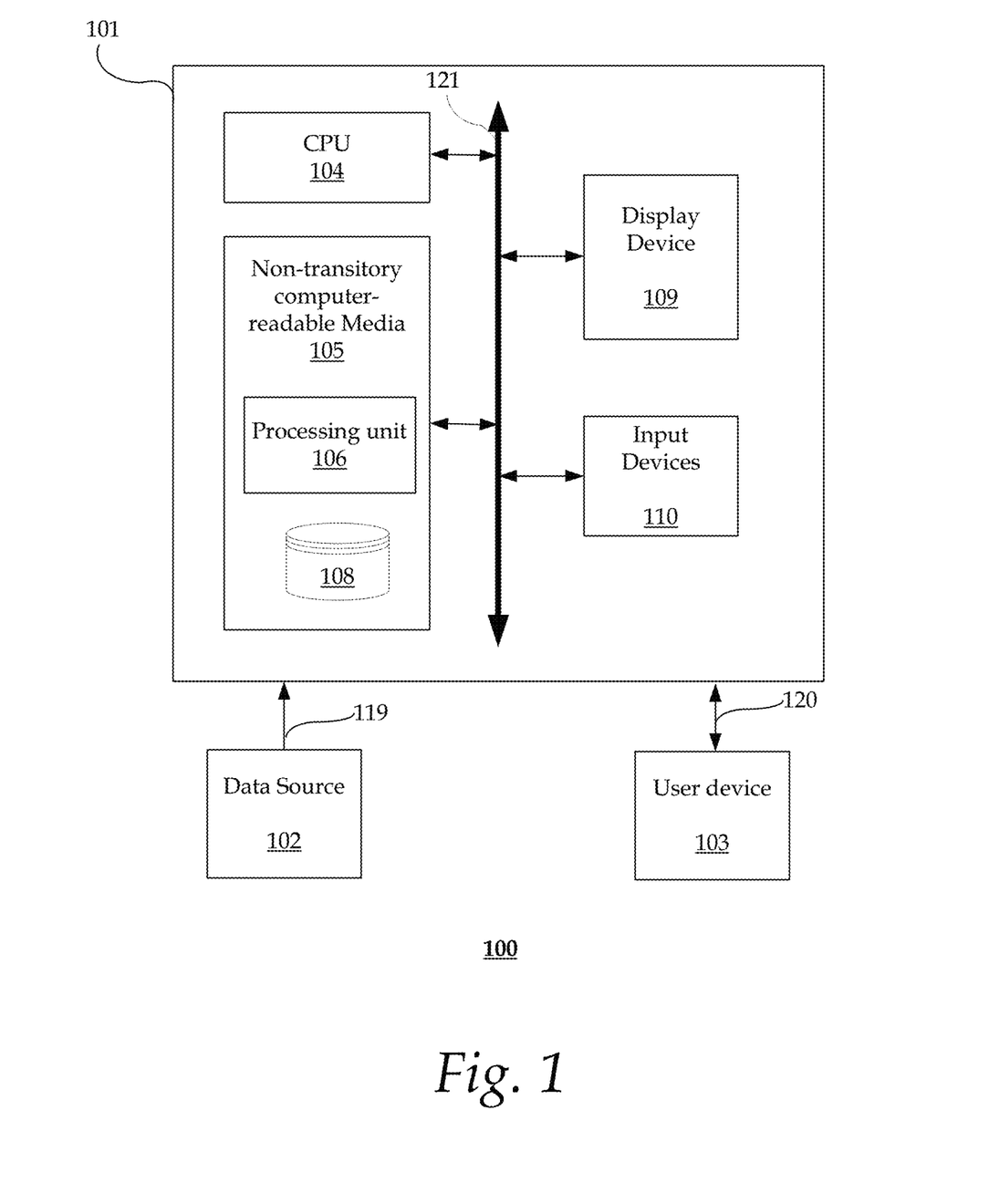
FIG. 1 is a block diagram illustrating an exemplary system.

FIG. 1 is a block diagram illustrating an exemplary system 100. The system 100 includes a computer system 101 for implementing the framework as described herein. In some implementations, computer system 101 operates as a standalone device. In other implementations, computer system 101 may be connected (e.g., using a network) to other machines, such as user device 103. In a networked deployment, computer system 101 may operate in the capacity of a server (e.g., thin-client server, such as Syngo.via® by Siemens Healthcare), a cloud computing platform, a client user machine in server-client user network environment, or as a peer machine in a peer-to-peer (or distributed) network environment.

In one implementation, computer system 101 comprises a processor or central processing unit (CPU) 104 coupled to one or more non-transitory computer-readable media 105 (e.g., computer storage or memory), display device 109 (e.g., monitor) and various input devices 110 (e.g., mouse or keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein are implemented as computer-readable program code tangibly embodied in non-transitory computer-readable media 105. In particular, the present techniques may be implemented by processing unit 106. Non-transitory computer-readable media 105 may include random access memory (RAM), read-only memory (ROM), magnetic floppy disk, flash memory, and other types of memories, or a combination thereof. The computer-readable program code is executed by CPU 104 to process data. As such, the computer system 101 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 105 may be used for storing a database (or dataset) 108. Such data may also be stored in external storage or other memories. The external storage may be implemented using a database management system (DBMS) managed by the CPU 104 and residing on a memory, such as a hard disk, RAM, or removable media. The external storage may be implemented on one or more additional computer systems. For example, the external storage may include a data warehouse system residing on a separate computer system, a picture archiving and communication system (PACS), or any other now known or later developed hospital, medical institution, medical office, testing facility, pharmacy or other medical patient record storage system.

The data source 102 may provide data 119 for processing by processing unit 106. Such data may include healthcare guidelines, publications, expert opinions, and/or patient records (e.g., radiology reports, image data, prior examination reports, diagnostic data, treatment plans, treatment outcomes, and other patient-specific information). Such data may be processed by processing unit 106 and stored in database 108. Data source 102 may be a computer, memory device, a radiology scanner (e.g., X-ray or a CT scanner) and/or appropriate peripherals (e.g., keyboard and display device) for acquiring, inputting, collecting, generating and/or storing such data.

User device 103 may include a computer (e.g., mobile computing device) and appropriate peripherals, such as a keyboard and display device, and can be operated in conjunction with the entire system 100. User device 103 may include a graphical user interface to present the visualization 120 generated by processing unit 106 and collect current patient records or input data for manipulating data processing by processing unit 106. User input data may be received via an input device (e.g., keyboard, mouse, touch screen voice or video recognition interface, etc.).

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2:
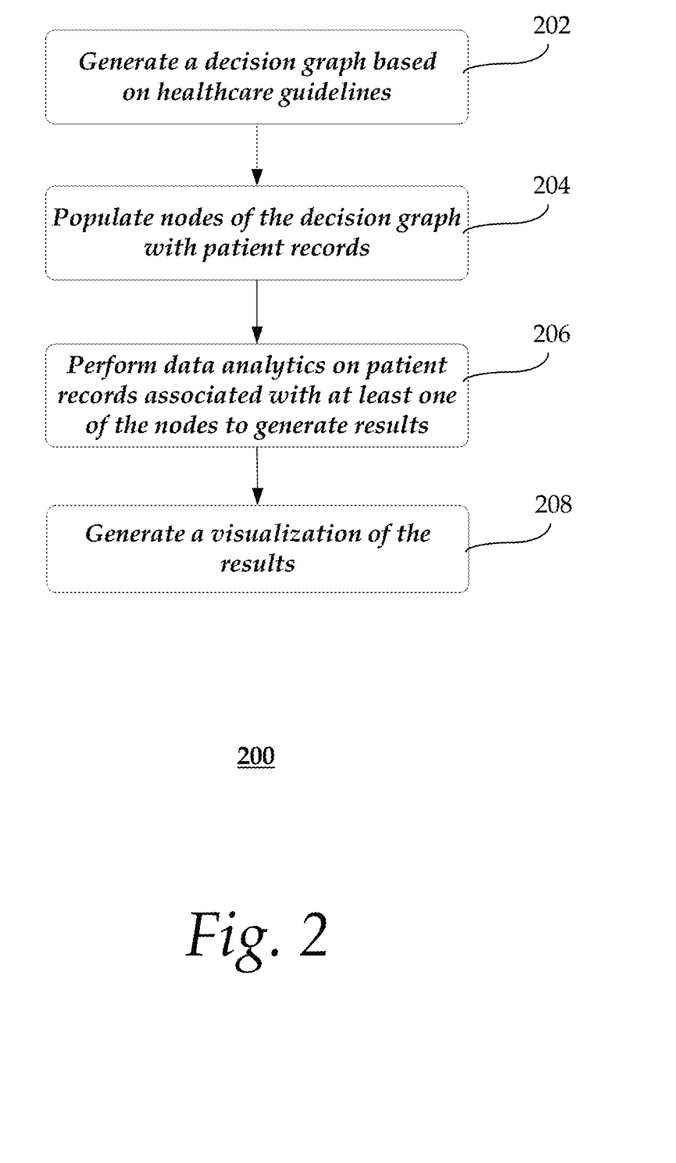
FIG. 2 shows an exemplary method of generating a visualization.

FIG. 2 shows an exemplary method 200 of generating a visualization by a computer system. It should be understood that the steps of the method 200 may be performed in the order shown or a different order. Additional, different, or fewer steps may also be provided. Further, the method 200 may be implemented with the system 101 of FIG. 1, a different system, or a combination thereof.

At 202, processing unit 106 generates a decision graph based on healthcare guidelines. Healthcare guidelines (also known as medical guidelines or clinical guidelines) generally refer to rules that guide decisions and criteria regarding diagnosis, management and/or treatment in specific areas of healthcare.

In some implementations, the healthcare guidelines comprise evidenced-based guidelines such as the appropriate use criteria (AUC), also known as appropriateness criteria. AUC define patient subgroups where the available medical evidence supplemented by expert opinion are combined to assess whether the net benefit or risks of a test or procedure make it reasonable to perform testing in a particular clinical situation. A technical panel may be engaged to score each procedure using the standardized rating scheme as follows: (1) Appropriate (Score 7-9): the use of the procedure is appropriate for the specific indication and is generally considered acceptable; (2) Uncertain (Score 4-6): The use of the procedure is uncertain for the specific indication, although its use may be appropriate and acceptable; and (3) Inappropriate (Score 1-3): Use of the procedure is inappropriate for the specific indication and generally is not considered acceptable.

In other implementations, the healthcare guidelines comprise a Care Process Model (CPM). A CPM are developed using evidence-based guidelines for healthcare providers to be used as a guide to administer medical care. A CPM summarizes clinical literature and provides expert advice regarding the diagnosis and management of certain diseases (e.g., asthma, depression, bipolar disorder, bronchitis, hypertension etc.).

Processing unit 106 may generate an electronic or digital representation of a decision graph based on the healthcare guidelines. The decision graph may include a tree-like diagram (or model) of decisions and their possible consequences. In some instances, the decision graph is a decision tree with leaf (or terminal) nodes. The decision graph may also include closed paths with no leaf nodes. Each node represents or contains a patient cohort.

The internal (or non-terminal) nodes of the decision graph may be a decision node or a recommendation node. A decision node may represent a particular test, question or investigation (e.g., whether symptoms of Ischemic Equivalent are present) of one or more attributes. Each branch from the decision node represents the outcome of the test, question or investigation. A recommendation node may represent a particular action (e.g., therapy, drug prescription, surgery, further testing or imaging) or inaction (e.g., wait and observe). The path from the root to a current node represents decisions, outcomes and/or recommendations for the particular patient cohort associated with the current node up until the current step of their healthcare case history. The leaf (or terminal) node may represent a conclusion (e.g., a particular procedure is appropriate or inappropriate for a particular patient cohort).

At 204, processing unit 106 populates nodes of the decision graph with the patient records. As the processing unit 106 populates the decision graph, pointers that reference the associated patient records (e.g., database entries or files) may be stored in an index file or other data structure. Each patient record includes (real or actual) data associated with an individual patient that may describe the patient's medical history and care across time. The patient record identifies the patient and contains information regarding the patient's case, including but not limited to, the patient's demographic information (e.g., age, gender, weight, ethnicity occupation, health insurance), surgical history, obstetric history, family history, previous and current medications, allergies, social history, habits, immunization history, developmental history, examination report, prescriptions, test results, medical image data, data recorded by wearable technology, and other types of health information.

The nodes may be populated by pushing (or advancing) a patient record along a path down the decision graph. The patient record may be pushed along a branch from a current node to the next level node in response to the patient record providing the outcome of the test represented by the branch. For example, the processing unit 106 may automatically populate the nodes by parsing the patient record to determine one or more attribute values (e.g., test result or measurement value) that represent the outcome of the test, question or investigation of a decision node and associating the patient record to the node that corresponds to the outcome. Alternatively, the processing unit 106 may present a user interface (e.g., graphical user interface) that enables the user to input the outcome of the test and associate the patient record to the node that represents the outcome. Accordingly, as each patient record lands on a particular node during the traversal of the decision graph, it is associated with (i.e., populates) that node. The path may be terminated at a leaf node, or a node associated with a test for which an outcome cannot be determined (e.g., insufficient data, test not performed, inconclusive results).

As the decision graph is used by the same or different healthcare practitioners, patient records are accumulated onto the nodes of the decision graph. A total count of the number of patient records at each interior node of the decision graph may be calculated and displayed in substantially real time. Other statistical values may also be updated and displayed. In some implementations, the nodes of the decision graph are updated in substantially real time with current patient records while being accessed by one or more users (e.g., healthcare practitioner or clinician) during, for example, examination or diagnosis of one or more current patients. Alternatively, the nodes are updated with patient records in pre-defined time intervals (e.g., daily or weekly).

At 206, processing unit 106 performs data analytics on patient records associated with at least one of the nodes to generate results. Data analytics is the discovery, organization, interpretation and/or communication of meaningful patterns in data (or attribute values) extracted from the patient records. Data analytics may be performed by invoking, for example, a statistical tool, a clustering algorithm, a classification technique, a prediction method, performance sensitivity analytical tool on node splitting criteria to determine how confident or confusing a split is, and so forth.

For example, a clustering technique may be applied to group a population of patient records into clusters according to similar attribute values (e.g., gender, age, family history, diagnosis, measurement value, measurements from wearable devices or smart phones, laboratory results, demographic, genetic or proteomic data, molecular diagnostic data, etc.). As another example, a statistical tool may be invoked to determine the total number of patients associated with the node, the average age of the patients, the man to woman ratio of the patients, or other statistical values. It should be appreciated that any other type of data analytics tool may also be applied. The control parameters of the analytical tool may be configured or selected by the user (e.g., physician, administrator) via a user interface at, e.g., user device 103.

Data analytics may be performed on any node in the decision graph. In some implementations, data analytics is performed on a node that has been selected by the user via a user interface. The decision graph may be displayed on, for example, a user device 103 via a graphical user interface. When the decision graph is displayed on a display device to the end user, the graphical user interface may enable the user to select (e.g., click) a node of the decision graph, and display all patient records associated with that node in response to the user selection At 208, processing unit 106 generates a visualization of the analytics results. In some implementations, the visualization is presented in a dashboard or dashboard-like environment. The visualization may be one-dimensional, two-dimensional or three-dimensional. The visualization may represent the analytics results in the form of a list, table (i.e., rows or columns with categorical labels) or graph (e.g., scatterplot, bar chart, histogram, pie chart, statistical distribution, line graph). The patient records may be displayed in a two-dimensional (2D) or three-dimensional (3D) graphical space with selectable axes representing attributes associated with the patient records. In a scatter graph (or scatter plot), for example, patient records are displayed as a collection of points (or other icons), each having the value of one attribute determining the position on the horizontal axis and the value of the other attribute determining the position on the vertical axis. Examples of various attributes that may be represented by the axes include, but are not limited to, age, gender, weight, family history, genetic information, ethnicity, ejection fraction of the left ventricle, or any other numerical or categorical descriptors.

In some implementations, the user interface enables the user to select or configure one or more attributes associated with the patient records that are processed by the data analytics tool and represented in the visualization. Alternatively, the one or more attributes may be pre-selected. In an exemplary user case, a user (e.g., physician or medical practitioner) may be interested in seeking clinical decision support for a particular patient associated with a current patient record. The visualization may present a comparison of the current patient record in relation to the population of patient records associated with a selected node with respect to one or more attributes. For example, the visualization may present the current patient record in a cluster of patient records that are most similar based on one or more attributes. In addition, the user may select one or more most similar patient records (i.e., most proximate neighbors) for further investigation. The visualization may present a comparison of the current patient record with the most similar patient records. Patient data may be extracted from the most similar patient records and presented in the visualization to support clinical decision making. The patient data may include, for example, administered treatments, interventions and/or outcomes. Such patient data may provide information to guide the user in administering healthcare to the patient, such as the type of treatment to use, follow-up choices, which intervention yields the best outcome and so forth.

In other instances, the user interface enables the user to select one or more sub-populations of patient records associated with the selected node to be processed by the data analytics tool and represented in the visualization. For example, a user (e.g., chief medical officer of a hospital) may be interested in evaluating the decisions made by medical practitioners in his or her organization to determine if there is any systematic bias or outliers. The user may select a first sub-set of patient records associated only with the particular organization to perform the data analytics. The user may further select another second sub-set or full set of patient records to provide the baseline for comparison. The visualization may then present a comparison of attribute values associated with the first subset of patient records with attribute values associated with the second subset or entire set of patient records associated with the selected node. The user may inspect the visualization to determine if there is any systematic bias or outliers. Alternatively, the processing unit 106 may automatically determine and indicate any systematic error.

Figure 3:
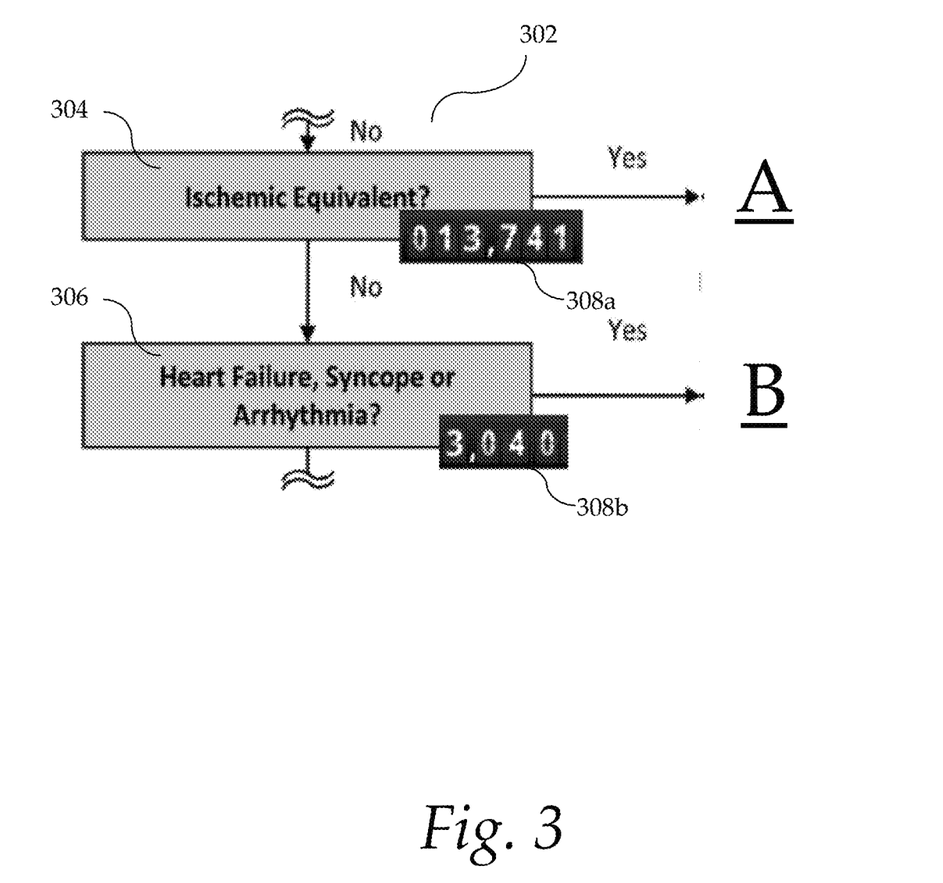
FIG. 3 shows an exemplary visualization of a portion of a decision graph.

FIG. 3 shows an exemplary visualization 302 of a portion of a decision graph. The decision graph is generated based on an echocardiography AUC. Node 304 represents a test on whether symptoms of "Ischemic Equivalent" are present, while node (306) represents a test on whether "heart failure, syncope or arrhythmia" is detected. The total number of patient records associated with each node (304 or 306) respectively are represented by a counter (308a or b). The counter may be updated in substantially real time as the decision graph is accessed by different users (e.g., physicians or healthcare practitioners). Alternatively, the counter may be updated at pre-determined time intervals (e.g., daily or weekly). Each node (304, 306) may branch to another decision graph (A or B). The user may view each of these decision graphs by making a selection.

Figure 4:
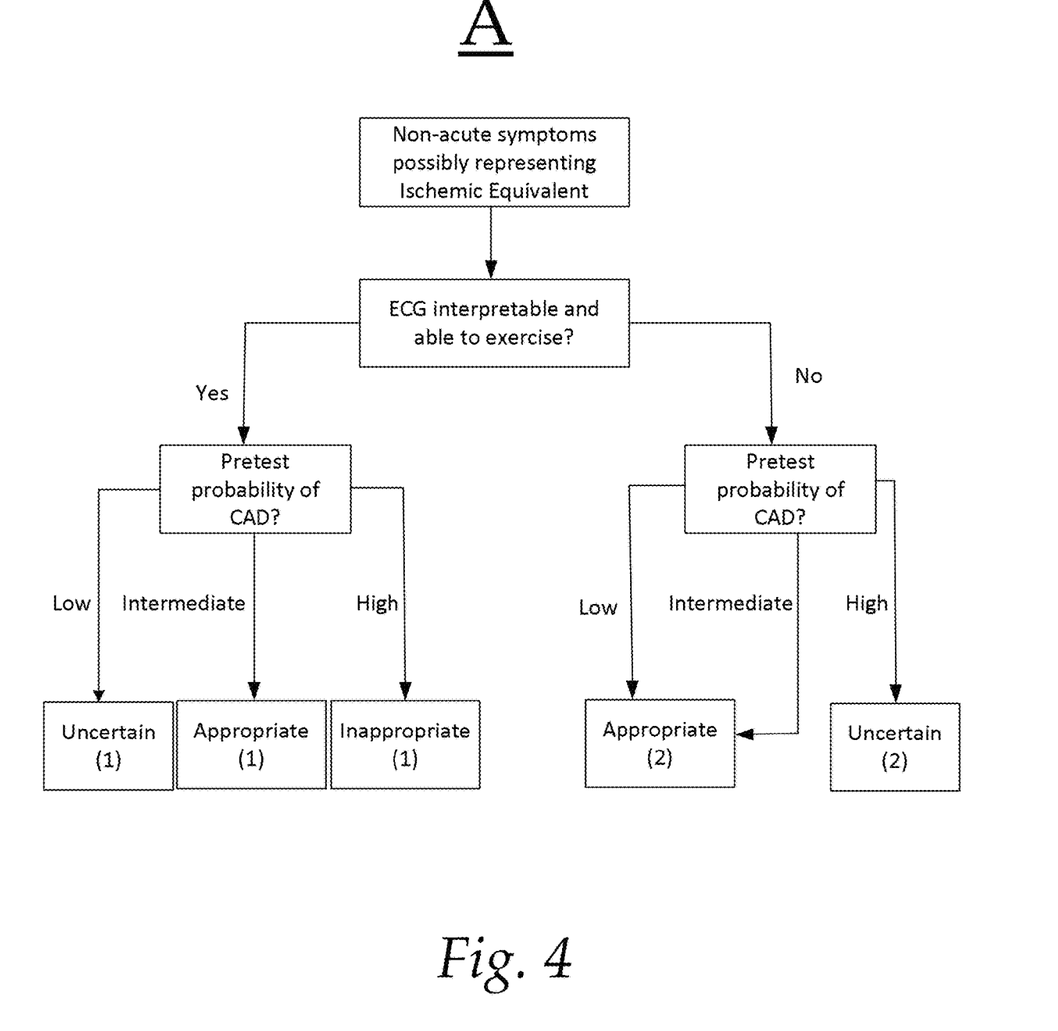
FIG. 4 shows an exemplary decision graph A.
Figure 5:
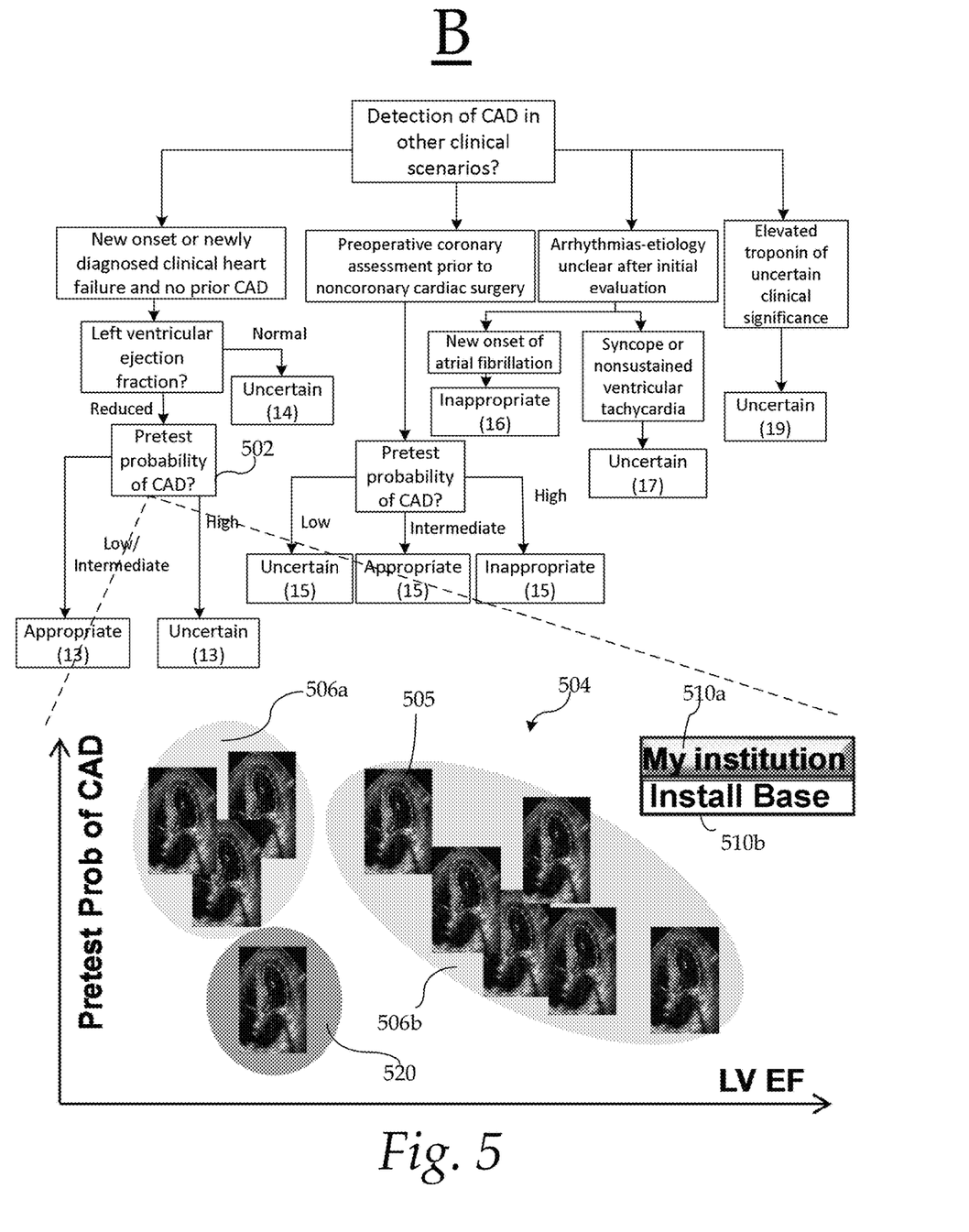
FIG. 5 shows an exemplary decision graph B.

FIG. 4 shows an exemplary AUC decision graph A for determining the appropriateness of using cardiac computed tomography (cCT) scans to assess non-acute symptoms possibly representing Ischemic Equivalent. FIG. 5 shows another exemplary AUC decision graph B for determining the appropriateness of using cCT to detect coronary artery disease (CAD) in other clinical scenarios. Each node of the decision graph (A or B) is associated with actual patient records. The user may view the patient records associated with the node by selecting the desired node. For example, by selecting node 502, the user may view a dashboard visualization 504 that presents results of data analytics performed on two selected sets of patient records associated with the node 502. As shown, the first set of patient records is associated with "My Institution" (510a) while the second set of patient records is associated with the entire "Install Base (IB)" (510b).

The dashboard 504 presents a scatterplot of patient records within a two-dimensional (2D) space defined by user-selected or user-configured axes. Each icon/image 505 represents a patient record associated with an individual patient. The vertical axis represents the pretest probability of CAD and the horizontal axis represents the ejection fraction of the left ventricle (LV EF). The user may invoke a clustering algorithm to generate new cluster structures (506a-506b). Sensitivity or confidence of a decision may be analyzed based on the clusters (506a-506b) and the spread of the patient records and cluster structures around the current patient record 520. Through usage, the graph becomes more quantitative and can be refined and updated based on accumulated data.

In some implementations, processing unit 106 traverses the decision graph in response to receiving a current patient record associated with a current patient. The current patient may be any individual that is currently undergoing examination or diagnosis for one or more medical conditions. The current patient record may include, for example, preexisting medical conditions, demographic attributes, physical attributes, family history, habits, preexisting medical conditions, temporary symptoms, patient management history, therapy outcomes, administered diagnostic test results, and so forth.

The decision graph is traversed along a path determined by attribute values (e.g., test results) extracted from the current patient record. The path may continue along a branch from a current node to the next level node in response to the attribute values providing the outcome of the test represented by the branch. In some instances, a user interface (at, e.g., user device 103) highlights a traversal path of the current patient record down the decision graph. This allows the user to know which nodes are relevant to the current patient record, and enables the user to select the relevant node for performing data analytics. The path may be terminated at a leaf node, a decision node associated with a test, question or investigation for which an outcome cannot be determined (e.g., insufficient data, test not performed, inconclusive results), or a recommendation node associated with an action or inaction that is currently performed.

Processing unit 106 may further generate a recommendation based on the final node of the path to support a healthcare decision for the current patient. For example, if the final node is a recommendation node that represents a particular action (e.g., therapy, drug prescription, surgery, further testing or imaging) or inaction (e.g., wait and observe), the recommendation is to perform that particular action or inaction. As another example, if the final node is a decision node that represents a particular test, the recommendation may be to perform another test. The recommendation may be presented via the user interface.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A system comprising:
    a non-transitory memory device for storing computer readable program code; and
    a processor in communication with the memory device, the processor being operative with the computer readable program code to perform operations including
        generating a decision graph based on healthcare guidelines, wherein the healthcare guidelines comprise a care process model,
        while multiple users are accessing the decision graph, populating, in substantially real time, nodes of the decision graph with patient records associated with a population of different patients by parsing at least one of the patient records to determine one or more attribute values that represent an outcome, pushing the at least one of the patient records from a current node to a next level node of the decision graph in response to the patient record providing the outcome represented by a branch from the current node to the next level node, and associating the at least one of the patient records with the next level node, and calculating and displaying, at the next level node, a total count of patient records associated with the next level node,
        automatically traversing the decision graph along a path determined by attribute values associated with a current patient record,
        performing data analytics on patient records associated with one or more nodes along the path to generate results, and
        generating a visualization of the results.

2. The system of claim 1 wherein the visualization comprises a comparison of the current patient record with one or more of the associated patient records that are most similar to the current patient record.

3. The system of claim 1 wherein the processor is operative with the computer readable program code to extract and present patient data from one or more of the associated patient records that are similar to the current patient record.

4. The system of claim 3 wherein the patient data comprises administered treatment, intervention, outcome or a combination thereof.

5. A non-transitory computer readable medium embodying a program of instructions executable by a machine to perform operations, the operations comprising:
    generating a decision graph based on healthcare guidelines, wherein the healthcare guidelines comprise a care process model;
    while multiple users are accessing the decision graph, populating, in substantially real time, nodes of the decision graph with patient records associated with a population of different patients by parsing at least one of the patient records to determine one or more attribute values that represent an outcome, pushing the at least one of the patient records from a current node to a next level node of the decision graph in response to the patient record providing the outcome represented by a branch from the current node to the next level node, and associating the at least one of the patient records with the next level node, and calculating and displaying, at the next level node, a total count of patient records associated with the next level node;
    performing data analytics on patient records associated with at least one of the nodes to generate results; and
    generating a visualization of the results.

6. The non-transitory computer readable medium of claim 5 wherein the instructions are executable by the machine to generate the visualization by highlighting a traversal path of a current patient record down the decision tree.

7. The non-transitory computer readable medium of claim 5 wherein the instructions are executable by the machine to parse the patient record to determine the outcome.

8. The non-transitory computer readable medium of claim 5 wherein the instructions are executable by the machine to present a user interface that enables a user to input the outcome.

9. The non-transitory computer readable medium of claim 5 wherein the healthcare guidelines comprise appropriate use guidelines.

10. The non-transitory computer readable medium of claim 5 wherein the instructions are executable by the machine to perform data analytics on the patient records by invoking a statistical tool, a clustering algorithm, a classification technique, a prediction method, a performance sensitivity analytical tool, or a combination thereof.

11. The non-transitory computer readable medium of claim 5 wherein the visualization comprises a list, table or graph.

12. The non-transitory computer readable medium of claim 5 wherein the visualization comprises a comparison of attribute values extracted from a first subset of the associated patient records with a second subset of the associated patient records.

13. The non-transitory computer readable medium of claim 12 wherein the instructions are executable by the machine to enable a user to select the first and second sub sets.

14. The non-transitory computer readable medium of claim 5 wherein the visualization comprises a comparison of attribute values extracted from a subset of the associated patient records with attribute values extracted from all the associated patient records.

15. A method, comprising:
generating a decision graph based on healthcare guidelines, wherein the healthcare guidelines comprise a care process model;
while multiple users are accessing the decision graph, populating, in substantially real time, nodes of the decision graph with patient records associated with a population of different patients by parsing at least one of the patient records to determine one or more attribute values that represent an outcome, pushing the at least one of the patient records from a current node to a next level node of the decision graph in response to the patient record providing the outcome represented by a branch from the current node to the next level node, and associating the at least one of the patient records with the next level node, and calculating and displaying, at the next level node, a total count of patient records associated with the next level node;
automatically traversing the decision graph along a path determined by attribute values associated with a current patient record; and
generating a recommendation based on a final node of the path to support a healthcare decision.

16. The method of claim 15 wherein generating the decision graph comprises generating a decision tree.

17. The method of claim 15 wherein generating the recommendation comprises generating a recommendation to perform a therapy, drug prescription, surgery, further testing or imaging, wait and observe, or a combination thereof.

* * * * *